United States Patent
Kladakis et al.

(10) Patent No.: US 8,657,881 B2
(45) Date of Patent: Feb. 25, 2014

(54) MENISCAL REPAIR SCAFFOLD

(75) Inventors: Stephanie M. Kladakis, Watertown, MA (US); Steven M. Bowman, Sherborn, MA (US); Robert R. Steckel, Norwalk, CT (US)

(73) Assignee: DePuy Mitek, LLC, Raynham, MA (US)

( * ) Notice: Subject to any disclaimer, the term of this patent is extended or adjusted under 35 U.S.C. 154(b) by 1626 days.

(21) Appl. No.: 10/828,841

(22) Filed: Apr. 20, 2004

(65) Prior Publication Data

US 2005/0234549 A1 Oct. 20, 2005

(51) Int. Cl.
*A61F 2/38* (2006.01)

(52) U.S. Cl.
USPC ..................................... 623/14.12

(58) Field of Classification Search
USPC ..................................... 623/14.12
See application file for complete search history.

(56) References Cited

U.S. PATENT DOCUMENTS

| | | |
|---|---|---|
| 206,200 A | 7/1878 | Stewart |
| 224,226 A | 2/1880 | Rind |
| 259,260 A | 6/1882 | Baeyer et al. |
| 3,812,017 A | 5/1974 | Santangelo et al. |
| 3,857,932 A | 12/1974 | Shepherd et al. |
| 4,520,821 A | 6/1985 | Schmidt et al. |
| 4,553,272 A | 11/1985 | Mears |
| 4,597,766 A | 7/1986 | Hilal |
| 4,609,551 A | 9/1986 | Caplan et al. |
| 4,790,819 A * | 12/1988 | Li et al. ............................. 604/59 |
| 4,801,299 A | 1/1989 | Brendel et al. |
| 4,902,508 A | 2/1990 | Badylak et al. |
| 4,952,404 A * | 8/1990 | Vallee et al. ................... 424/422 |
| 5,007,934 A | 4/1991 | Stone |
| 5,041,138 A | 8/1991 | Vacanti et al. |
| 5,053,050 A | 10/1991 | Itay |
| 5,061,281 A | 10/1991 | Mares et al. |
| 5,108,989 A | 4/1992 | Amento et al. |
| 5,147,400 A | 9/1992 | Kaplan et al. |
| 5,206,023 A | 4/1993 | Hunziker |
| 5,326,357 A | 7/1994 | Kandel |
| 5,425,766 A | 6/1995 | Bowald |
| 5,443,950 A | 8/1995 | Naughton et al. |

(Continued)

FOREIGN PATENT DOCUMENTS

| | | |
|---|---|---|
| DE | 198 12 195 | 9/1999 |
| EP | 0 274 898 | 7/1988 |

(Continued)

OTHER PUBLICATIONS

Thomas F. Deuel and Nan Zhang, "Growth Factors" in Principles of Tissue Engineering, Second Edition, Academic Press, 2000, pp. 129-141.

(Continued)

*Primary Examiner* — Thomas J Sweet
*Assistant Examiner* — Megan Wolf

(57) ABSTRACT

Methods and apparatus for treating meniscal tissue damage are disclosed, including a biocompatible meniscal repair device comprising a biocompatible tissue repair scaffold and a cell growth conduit flap. The tissue repair scaffold is adapted to be placed in contact with a defect in the meniscus and can preferably provide a structure for supporting meniscal tissue and/or encouraging tissue growth. The cell growth conduit flap, which is attached to the tissue repair scaffold, allows communication between the synovium and the tissue repair scaffold.

13 Claims, 5 Drawing Sheets

(56) References Cited

U.S. PATENT DOCUMENTS

| | | | |
|---|---|---|---|
| 5,445,833 A | 8/1995 | Badylak et al. |
| 5,455,041 A | 10/1995 | Genco et al. |
| 5,480,827 A | 1/1996 | Guillemin et al. |
| 5,514,181 A | 5/1996 | Light et al. |
| 5,577,517 A | 11/1996 | Bonutti |
| 5,632,745 A | 5/1997 | Schwartz |
| 5,677,355 A | 10/1997 | Shalaby et al. |
| 5,681,353 A | 10/1997 | Li et al. |
| 5,709,854 A | 1/1998 | Griffith-Cima et al. |
| 5,720,969 A | 2/1998 | Gentile et al. |
| 5,723,331 A | 3/1998 | Tubo et al. |
| 5,736,372 A | 4/1998 | Vacanti et al. |
| 5,755,791 A | 5/1998 | Whitson et al. |
| 5,759,190 A | 6/1998 | Vibe-Hansen et al. |
| 5,766,631 A | 6/1998 | Arnold |
| 5,769,899 A | 6/1998 | Schwartz et al. |
| 5,786,217 A | 7/1998 | Tubo et al. |
| 5,830,493 A | 11/1998 | Yokota et al. |
| 5,837,235 A | 11/1998 | Mueller et al. |
| 5,842,477 A | 12/1998 | Naughton et al. |
| 5,891,558 A | 4/1999 | Bell et al. |
| 5,902,741 A | 5/1999 | Purchio et al. |
| 5,904,716 A | 5/1999 | Gendler |
| 5,904,717 A | 5/1999 | Brekke et al. |
| 5,914,121 A | 6/1999 | Robey et al. |
| 5,964,805 A | 10/1999 | Stone |
| 5,968,096 A | 10/1999 | Whitson et al. |
| 5,980,889 A | 11/1999 | Butler et al. |
| 5,989,269 A | 11/1999 | Vibe-Hansen et al. |
| 5,990,194 A | 11/1999 | Dunn et al. |
| 5,990,378 A | 11/1999 | Ellis |
| 6,001,352 A | 12/1999 | Boyan et al. |
| 6,001,394 A | 12/1999 | Daculsi et al. |
| 6,005,161 A | 12/1999 | Brekke et al. |
| 6,027,742 A | 2/2000 | Lee et al. |
| 6,080,579 A | 6/2000 | Hanley, Jr. et al. |
| 6,096,532 A | 8/2000 | Armstrong et al. |
| 6,103,255 A | 8/2000 | Levene et al. |
| 6,110,209 A | 8/2000 | Stone |
| 6,120,514 A | 9/2000 | Vibe-Hansen et al. |
| 6,121,042 A | 9/2000 | Peterson et al. |
| 6,123,727 A | 9/2000 | Vacanti et al. |
| 6,132,463 A | 10/2000 | Lee et al. |
| 6,139,578 A | 10/2000 | Lee et al. |
| 6,140,039 A | 10/2000 | Naughton et al. |
| 6,143,293 A | 11/2000 | Weiss et al. |
| 6,153,292 A | 11/2000 | Bell et al. |
| 6,179,872 B1 | 1/2001 | Bell et al. |
| 6,180,007 B1 | 1/2001 | Gentile et al. |
| 6,183,737 B1 | 2/2001 | Zaleske et al. |
| 6,187,053 B1 | 2/2001 | Minuth |
| 6,197,061 B1 | 3/2001 | Masuda et al. |
| 6,200,606 B1 | 3/2001 | Peterson et al. |
| 6,214,045 B1 | 4/2001 | Corbitt, Jr. et al. |
| 6,251,673 B1 | 6/2001 | Winkler |
| 6,277,151 B1 | 8/2001 | Lee et al. |
| 6,283,980 B1 | 9/2001 | Vibe-Hansen et al. |
| 6,287,340 B1 | 9/2001 | Altman et al. |
| 6,291,240 B1 | 9/2001 | Mansbridge et al. |
| 6,306,424 B1 | 10/2001 | Vyakarnam et al. |
| 6,319,712 B1 | 11/2001 | Meenen et al. |
| 6,331,312 B1 | 12/2001 | Lee et al. |
| 6,365,149 B2 | 4/2002 | Vyakarnam et al. |
| 6,379,367 B1 | 4/2002 | Vibe-Hansen et al. |
| 6,468,314 B2 * | 10/2002 | Schwartz et al. ......... 623/23.72 |
| 6,511,958 B1 | 1/2003 | Atkinson et al. |
| 6,541,024 B1 | 4/2003 | Kadiyala et al. |
| 6,599,323 B2 | 7/2003 | Melican et al. |
| 6,605,294 B2 | 8/2003 | Sawhney |
| 7,901,461 B2 | 3/2011 | Harmon et al. |
| 8,137,686 B2 | 3/2012 | Kladakis et al. |
| 8,221,780 B2 | 7/2012 | Dhanaraj et al. |
| 2001/0016353 A1 | 8/2001 | Janas et al. |
| 2001/0023373 A1 | 9/2001 | Plouhar et al. |
| 2001/0039453 A1 | 11/2001 | Gresser et al. |
| 2001/0053353 A1 | 12/2001 | Griffith et al. |
| 2001/0053839 A1 | 12/2001 | Noishiki et al. |
| 2002/0009805 A1 | 1/2002 | Nevo et al. |
| 2002/0009806 A1 | 1/2002 | Hicks, Jr. |
| 2002/0028192 A1 | 3/2002 | Dimitrijevich et al. |
| 2002/0029055 A1 | 3/2002 | Bonutti |
| 2002/0062151 A1 | 5/2002 | Altman |
| 2002/0082631 A1 | 6/2002 | Bonutti |
| 2002/0091403 A1 | 7/2002 | Bonutti |
| 2002/0091406 A1 | 7/2002 | Bonutti |
| 2002/0099401 A1 | 7/2002 | Bonutti |
| 2002/0099448 A1 | 7/2002 | Hiles et al. |
| 2002/0107570 A1 | 8/2002 | Sybert et al. |
| 2002/0127265 A1 | 9/2002 | Bowman et al. |
| 2002/0133229 A1 | 9/2002 | Laurencin et al. |
| 2002/0173558 A1 | 11/2002 | Williams et al. |
| 2003/0026787 A1 | 2/2003 | Fearnot et al. |
| 2003/0036797 A1 * | 2/2003 | Malaviya et al. ......... 623/14.12 |
| 2003/0044444 A1 * | 3/2003 | Malaviya et al. ............ 424/423 |
| 2003/0077311 A1 | 4/2003 | Vyakarnam et al. |
| 2004/0143344 A1 * | 7/2004 | Malaviya et al. ......... 623/23.72 |
| 2005/0177249 A1 | 8/2005 | Kladakis et al. |

FOREIGN PATENT DOCUMENTS

| | | |
|---|---|---|
| EP | 0 562 864 | 9/1993 |
| EP | 0 955 024 | 11/1999 |
| EP | 1 064 958 | 1/2001 |
| EP | 1 167 517 | 1/2002 |
| EP | 1 216 718 | 6/2002 |
| EP | 1 405 649 | 4/2004 |
| RU | 2187261 | 8/2002 |
| SU | 1535542 | 1/1990 |
| WO | WO 86/00533 | 1/1986 |
| WO | WO 95/33821 | 12/1995 |
| WO | WO 97/30662 | 8/1997 |
| WO | WO 97/46665 | 12/1997 |
| WO | WO 98/48860 | 11/1998 |
| WO | WO 99/16381 | 4/1999 |
| WO | WO 99/47097 | 9/1999 |
| WO | WO 01/85226 | 11/2001 |

OTHER PUBLICATIONS

Sally R. Frenkel, Ph.D. and Paul E. Di Cesare, M.D., "Degradation and Repair of Articular Cartilage" in Frontiers in Bioscience, $4^{th}$ ed., pp. 671-685, Oct. 15, 1999, pp. 1-32.

Keith J. Gooch et al., "Mechanical Forces and Growth Factors Utilized in Tissue Engineering" in Frontier in Tissue Engineering, Pergamon, 1998, Chapter 11.3, pp. 61-82.

John A. Koski, M.D. et al., "Meniscal Injury and Repair", Orthopedic Clinics of North American, vol. 31, No. 3, Jul. 2000, pp. 419-435.

John A. Koski, M.D. et al., "Tissue-Engineered Ligament—Cells, Matrix, and Growth Factors" in Tissue Engineering in Orthopedic Surgery, vol. 31, No. 3, Jul. 2000, pp. 437-452.

Clemente Ibarra, M.D. et al. "Tissue-Engineered Meniscus—Cells and Matrix", in Tissue Engineering in Orthopedic Surgery, vol. 31, No. 3, Jul. 2000, pp. 411-418.

Stone, K. et al. "Meniscal Regeneration With Copolymeric Collagen Scaffolds" American Journal of Sports Medicine, 20(2):104-111 (1992).

Murray, M., et al. "The Migration of Cells from the Rup[tured Human Anterior Cruciate Ligament into Collagen-Glycosaminoglycan Regeneration Templated in Vitro" Biomaterials 22:2393-2402 (2001).

(Abstract Only) Caterson EJ., et al. "Three-Dimensional Cartilage Formation by Bone Marrow-Derived Cells Seeded in Polylactide/Alginate Amalgam" J Biomed Mater Res, 57(3):394-403 (2001).

(Abstract Only) Grigolo, B., et al. "Transplantation of Chondrocytes Seeded on a Hyaluronan Derivative (hyaff-11) into Cartilage Defects in Rabbits" Biomaterials 22(17):2417-2424 (2001).

(Abstract Only) van Susante JLC, et al. "Linkage of Chondroitin-sulfate to Type I Collagen Scaffolds Stimulates the Bioactivity of Seeded Chondrocytes in Vitro", Biomaterials, 22(17):2359-2369 (2001).

(56) References Cited

OTHER PUBLICATIONS (Abstract Only) Hutmacher DW., "Scaffold Design and Fabrication Technologies for Engineering Tissues-State of the Art and future Prospectives", J Biomater Sci Polym Ed, 12(1):107-124 (2001).
(Abstract Only) Hutmacher DW., "Scaffolds in Tissue Engineering Bone and Cartilage", Biomaterials, 21(24):2529-2543 (2000).
(Abstract Only) Schreiber RE., et al. "A Method for Tissue Engineering of cartilage by Cell Seeding on Bioresorbable Scaffolds" Ann NY Acad Sci, 875:394-404 (1999).
(Abstract Only) Radice, M. "Hyaluronan-Based Biopolymers as delivery vehicles for Bone-Marrow-Derived Mesenchymal Progenitors", J Biomed Mater Res, 50(2):101-9 (2000).
Albrecht, F., et al. Closure of Osteochondral Lesions Using Chondral Fragments and Fibrin Adhesive, Arch Orthop. Trauma Surg. (1983) 101:213-217.
Sampath, T.K., et al. In vitro transformation of mesenchymal cells derived from embryonic muscle into cartilage in response to extracellular matrix components of bone, Proc. Natl. Acad. Sci. USA vol. 81, pp. 3419-3423, Jun. 1984.
Bonisch, M., et al. "Septumredonstrucktion mit PDS-Folie" HNO 47: 1999 pp. 546-550.
Eckersberger, M.D., Franz, "Circumferential tracheal replacement with costal cartilage", The Journal of Thoracic and Cardiovascular Surgery, 1987;94: pp. 175-180.
Matsuo, M.D., Kiyoshi et al., "Semiquantitative Correction of Post-traumatic Enophthalmos with Sliced Cartilage Grafts" Plastic and Reconstructive Surgery, vol. 83, No. 3, Postraumatic Enophthalmos, pp. 429-437.
Megumi, M.D., Yoshikazu, "Augmentation Rhinoplasty with Soft Tissue and Cartilage" Aesthetic Plastic Surgery, 1988, pp. 89-933.
Papadopulos, M.D., Angel, "Compound Implant to Projedt the Nasal Tip" Aesthetic Plastic Surgery, 1987, pp. 181-185.
Partial European Search Report, for EP 04 25 7515, mailed May 9, 2005.
Powers, Dennis L. et al., "A cartilagenous graft as an adjunct to finger joint implant arthroplasty" Journal of Biomedical Materials Research, vol. 19, 1985 pp. 509-518.
Rohrbach, Jens Martin et al., "Biological Corneal Replacement—Alternative to Keratoplasty and Keratoprosthesis? A Pilot Study with Heterologous Hyaline Cartilage in the Rabbit Model", Klin Monatsbl Augenheilkd 207, 1995; pp. 191-196.
Trenite, M.D., G.J. Nolst et al., "Reimplantation of autologous septal cartilage in the growing nasal septum", Rhinology, 25, 1987, pp. 225-236.

\* cited by examiner

MENISCAL REPAIR SCAFFOLD

BACKGROUND OF THE INVENTION

The present invention generally relates to methods and apparatus for repairing meniscal defects, and in particular to tissue repair scaffold devices having an enhanced ability to promote cell growth.

The meniscus is specialized tissue found between the bones of a joint. For example, in the knee the meniscus is a C-shaped piece of fibrocartilage which is located at the peripheral aspect of the joint between the tibia and femur. This tissue performs important functions in joint health including adding joint stability, providing shock absorption, and delivering lubrication and nutrition to the joint. As a result, meniscal injuries can result in debilitating conditions including degenerative arthritis.

Meniscus injuries, and in particular tears, are a relatively common injury. Such injuries can result from a sudden twisting-type injury such as a fall, overexertion during a work-related activity, during the course of an athletic event, or in any one of many other situations and/or activities. In addition, tears can develop gradually with age. In either case, the tears can occur in either the outer thick part of the meniscus or through the inner thin part. While some tears may involve only a small portion of the meniscus, others affect nearly the entire meniscus.

Unfortunately, a damaged meniscus is unable to undergo the normal healing process that occurs in other parts of the body. The peripheral rim of the meniscus at the meniscosynovial junction is highly vascular (red zone) whereas the inner two-thirds portion of the meniscus is completely avascular (white zone), with a small transition (red-white zone) between the two. Degenerative or traumatic tears to the meniscus which result in partial or complete loss of function frequently occur in the white zone where the tissue has little potential for regeneration. Such tears result in severe joint pain and locking, and in the long term, a loss of meniscal function leading to osteoarthritis.

Although several treatments currently exist for meniscal injuries, the treatment options provide little opportunity for meniscal repair or regeneration. The majority of meniscal injuries are treated by removing the unstable tissue during a partial meniscectomy. Once the tissue is removed no further treatment is conducted. Most patients respond well to this treatment in the short term but often develop degenerative joint disease several years (i.e., after more than about 10 years) post operatively. The amount of tissue removed has been linked to the extent and speed of degeneration. When the majority of the meniscal tissue is involved in the injury, a total meniscectomy is conducted. If the patient experiences pain after a total meniscectomy without significant joint degeneration, a secondary treatment of meniscal allografts is possible. The use of allografts is limited by tissue availability and by narrow indications.

For meniscal tears that can be stabilized in vascularized areas of the meniscus, the tears can be repaired with suture or equivalent meniscal repair devices. While these repairs are successful in approximately 60-80% of the cases, the percentage of injuries which meet the criteria to be repaired is 15% or less. Repair criteria are based not only on vascularity and type of tear but also stability and integrity of the meniscus, stability of the knee and patient factors such as age and activity. If the repair does fail, the next possible course of treatment is either a partial or total meniscectomy.

Accordingly, there continues to exist a need in this art for novel tissue repair devices capable of encouraging meniscal tissue regeneration, as well as, methods for using such tissue repair devices.

SUMMARY OF THE INVENTION

The present invention provides methods and apparatus for treating damaged meniscal tissue, including a biocompatible meniscal repair device having a tissue repair scaffold and a cell growth conduit flap. The tissue repair scaffold is adapted to be placed in contact with a defect in the meniscus and it can provide a structure for supporting meniscal tissue and/or encouraging tissue growth. The cell growth conduit flap, which is attached to the tissue repair scaffold, communicates between the synovium and the tissue repair scaffold.

In one aspect of the invention, the cell growth conduit flap provides a conduit that enables biological materials, such as cells and nutrients, to travel from the synovium to the tissue repair scaffold and the meniscal defect. Preferably, these biological materials facilitate rapid and effective tissue regeneration at an injury or defect site which lacks vascularization.

In another aspect of the invention, the tissue repair scaffold and/or the cell growth conduit flap are constructed from bioabsorbable materials. In one embodiment, the tissue repair scaffold and the cell growth conduit flap are constructed from synthetic polymers derived from monomers selected from the group consisting of glycolide, lactide, and dioxanone. In yet another embodiment, the tissue repair scaffold and the cell growth conduit flap are constructed of the same material.

The meniscal repair device can preferably include viable tissue disposed on or within the tissue repair scaffold and effective to integrate with native tissue adjacent to the tissue repair scaffold. In addition, the tissue repair scaffold can include at least one bioactive substance effective to stimulate cell growth. Exemplary bioactive substances include platelet rich plasma, cartilage-derived morphogenic proteins, recombinant human growth factors, and combinations thereof.

In another aspect of the invention, the relative orientation of the cell growth conduit flap and the tissue repair scaffold is such that they form a "T" shape. Alternatively, the cell growth conduit flap and the tissue repair scaffold can be oriented so as to form a "L" shape.

In another aspect, the invention includes a method of surgically repairing meniscal defects by providing a meniscal repair device having attached thereto a cell growth conduit flap. The tissue repair scaffold is surgically placed in contact with a defect in a meniscus and the cell growth conduit flap is surgically placed in contact with the synovium. The cell growth conduit flap allows cells and nutrients from the synovium to travel to the defect in the meniscus and thereby encourage healing of the meniscus.

BRIEF DESCRIPTION OF THE DRAWINGS

The invention will be more fully understood from the following detailed description taken in conjunction with the accompanying drawings.

DETAILED DESCRIPTION OF THE INVENTION

The present invention provides a biocompatible meniscal repair device for use in surgically repairing defects or injuries to meniscal tissue. The device includes a biocompatible tissue repair scaffold adapted to be placed in contact with a defect in the meniscus and a cell growth conduit flap that is attached to the tissue repair scaffold, and that is effective to allow communication of materials between the synovium and the tissue repair scaffold.

Figure 1:
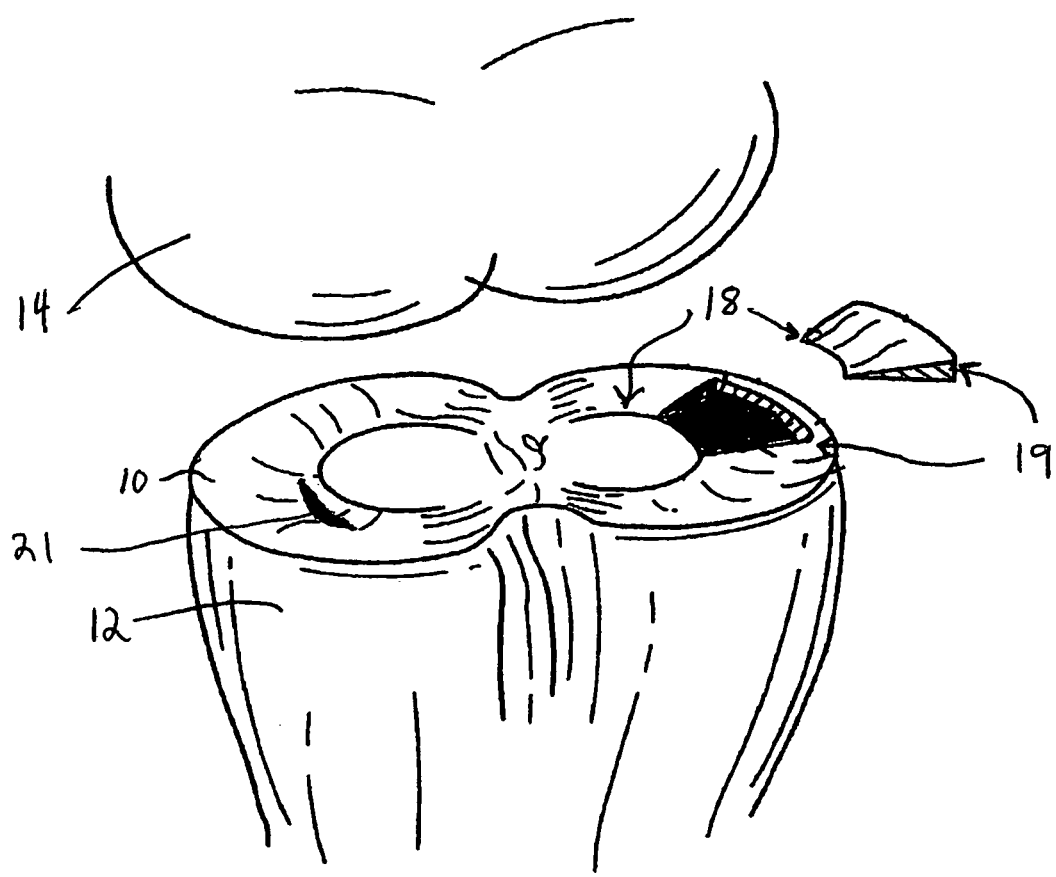
FIG. 1 illustrates an exploded view of the knee joint showing the meniscus.

The meniscus is found between the tibia and femur and provides a large surface of articulation between the otherwise incongruent surfaces of the tibial platform and the femoral condyles. FIG. 1 illustrates an exploded view of a knee with meniscus 10, tibia 12, and femur 14. A section of meniscus 10 is removed to show the generally wedged shaped cross-section between the thinner, inner white zone 18 and the outer, thicker red zone 19.

Injuries to meniscal tissue, such as meniscal tears 21, can develop throughout the meniscus. Unfortunately, meniscal injuries heal slowly, if at all, because of the demanding conditions within the knee joint and because of a typical lack of nutrients and fresh cells. This problem is particularly pronounced within the white zone 18 because of an almost complete lack of vascularization. While conventional treatments have required partial removal of damaged meniscal tissue, the present invention provides a device for supporting a meniscal tear and encouraging tissue regeneration.

With reference to FIGS. 2-5, the meniscal repair device 20 of the present invention includes a biocompatible tissue repair scaffold 22, which can support damaged tissue and act as a platform for new tissue growth, and a cell growth conduit flap 24 which facilitates the migration of cells and nutrients to the site of meniscal tissue damage.

Figure 2:
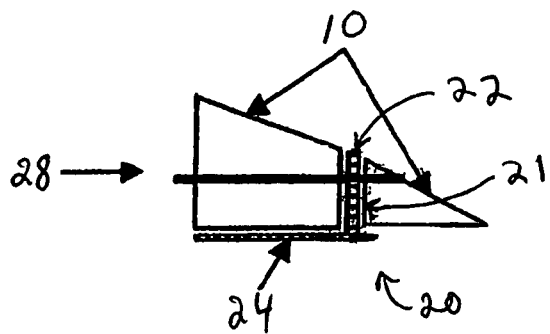
FIG. 2 is a side view of one embodiment of a meniscal repair device in accordance with the present invention.

FIG. 2 illustrates one embodiment of the meniscal repair device 20 of the present invention, with tissue repair scaffold 22 positioned in a defect within meniscal tissue so as to encourage tissue regeneration. To avoid the need for a meniscectomy, the scaffold 22 can, in one embodiment, be used to promote healing of torn meniscal tissue. For example, the scaffold can be inserted into a torn area 21 and sutured in place to stabilize loose meniscal tissue. With scaffold 22 fixed in place, further tearing can be reduced or eliminated and the scaffold can provide a matrix for cell growth.

Scaffold 22 can perform a variety of functions in addition to, or as an alternative to, tissue fixation. In one embodiment, scaffold 22 can provide a structure to encourage and guide new tissue growth. In addition, the scaffold can act as a vehicle for delivering a variety of materials to encourage tissue regeneration. Delivery of materials such as bioactive agents and cells to the damaged tissue may be particularly desirable.

Conduit flap 24, which is preferably adapted to rest on the tibial surface as shown in FIG. 2. can help to increase the mechanical stability of the implanted device. Meniscal implants are usually subject to forces within the knee joint that tend to push the device toward the femoral surface, and the conduit flap, which is positioned on the tibial side of the meniscus, can help to anchor the repair device in place. The conduit flap can be fixed in place to help secure the device, and in addition, the placement of the conduit flap on the tibial side of the meniscus preferably subjects it to opposing forces. Thus, the implanted device is less likely to slip out of the tissue defect site and disrupt tissue regeneration.

The conduit flap is also effective to provide a pathway for biological materials to reach damaged meniscal tissue, thus facilitating rapid healing of meniscal tears. In particular, the conduit flap can enable autologous biological materials such as cell nutrients, cells, lubricating fluids, and/or blood supply, to reach and/or be maintained at the scaffold and the injury site. These materials, which normally are unable to reach portions of the meniscus, are necessary for new tissue growth within the meniscus.

Conduit flap 24 can preferably extend from scaffold 22 so that it is able to access an area of increased vascularization such as the red zone or the tibial surface, and even more preferably, the conduit flap is able to extend to the synovium. The synovium produces and absorbs a clear synovial fluid which lubricates and feeds cartilage surfaces of the meniscus. The synovium also provides a robust source of viable cells and vascular supply. FIG. 2 shows an "L" shaped embodiment of repair device 20 where repair scaffold 22 and conduit flap 24 are oriented substantially perpendicular to one another and are joined at their intersection 26. The conduit flap is able to extend from meniscal tear 21 into the synovium, thereby creating a passage for synovial fluid, cells, and blood supply and other biological materials to reach the meniscal tear.

The material properties and structure of the conduit flap 24 allow the passage of biological materials. In one embodiment, the conduit flap creates a passageway as a result of its advantageously high level of porosity or void space. For example, an open pore structure or interconnectivity between the void spaces allows fluids and/or cells to move more easily through the conduit flap than the neighboring meniscus, which consists of dense, fibrous tissue. Furthermore, the porosity or void space in the scaffold provides for retention of biological materials traveling from the synovium and/or for implanted materials such as implanted bioactive substances.

In another embodiment, the conduit flap may include internal or external features which permit the passage of biological materials. For example, channels within the cell growth conduit flap or on the surface thereof, can allow synovial and other biological materials to reach tissue defects in the meniscus.

In yet another embodiment, the conduit flap can be adapted for drawing the biological materials toward the meniscal defect. For example, the conduit flap can contain materials which can wick liquids, such as, for example absorbent materials. When the conduit flap is positioned with one end in contact with the synovium, biological materials are then drawn toward the tissue scaffold and the injury site. Preferably, the conduit flap and/or the scaffold can retain the absorbed biological materials adjacent to the defect site.

Preferred material properties of the conduit flap include a density in the range of about 150 mg/cc to 350 mg/cc, and even more preferably 200 mg/cc to 275 mg/cc. In one embodiment, the conduit flap can be constructed from a synthetic, bioabsorbable polymeric material. An exemplary material may be constructed from synthetic polymer fibers having a diameter in the range of about 5 to 50 micrometers.

Other preferred properties of the conduit flap include tissue contact surfaces that are low or non-abrading such that the implant will cause minimal damage to adjacent cartilage. For example, the conduit flap can include low friction surfaces or coatings which minimize any damaged caused by movement between the implant and adjacent tissue.

Figure 3:
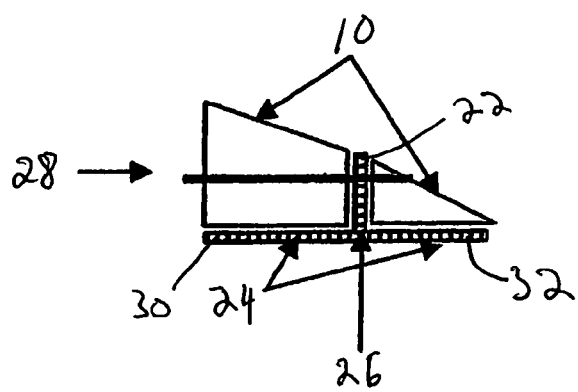
FIG. 3 is a side view of another embodiment of a meniscal repair device in accordance with the present invention.

FIG. 3 illustrates another embodiment of meniscal repair device 20 in which the scaffold and the conduit flap are oriented so as to have a "T" shape, in which the edge of scaffold 22 divides conduit flap 24 into first and second portions 30, 32. First portion 30 of the conduit flap 24, which is similar to the conduit flap in the "L" embodiment, extends into an area of increased vasularization. Second portion 32 extends into an area of limited vascularization. The second portion can provide support to meniscal tissue, particularly loose meniscal tissue, and also provide a conduit to communicate biological materials to additional areas of the meniscus.

In another embodiment, the meniscal repair device 20 can assist with regenerating lost meniscal tissue. Where part of the meniscus is destroyed or removed, the scaffold of the present invention can substitute for the missing meniscal tissue and thereby facilitate new cell growth. The scaffold, along with biological materials delivered via the conduit flap, provide an environment in which new cells can grow to regenerate missing meniscal tissue.

Figure 4:
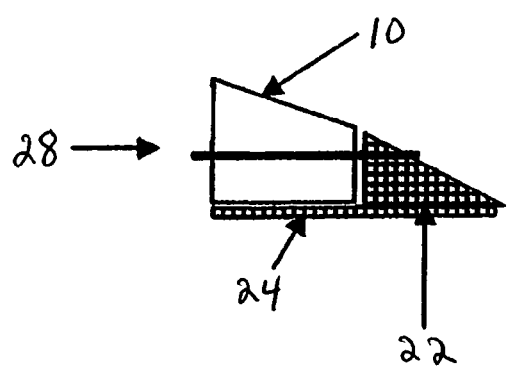
FIG. 4 is a side view of a meniscal repair device in accordance with another embodiment of the present invention.

FIG. 4 illustrates one such embodiment in which a wedge-shaped scaffold 22 is adapted to substitute for missing meniscal tissue. Conduit flap 24 is preferably attached to the scaffold 22 at a bottom portion, such that it extends from the scaffold toward the vascularized zone. Conduit flap 24 thus provides a pathway for the necessary nutrients, cells, lubrication, and/or other materials required for new tissue growth.

The meniscal repair device is preferably sized for positioning within the knee joint, and in particular, within a meniscal defect. The dimensions of the device will vary depending upon factors including the size and location of a meniscal defect. One skilled in the art will appreciate that a range of dimensions are possible. Preferably, the device is large enough to fill a defect to a suitable extent, while allowing the conduit flap to extend to the synovium. Conversely, the dimensions of the device, and in particular the conduit flap, are preferably small enough such that the device does not cause damage to tissue outside the knee joint capsule. For example, in one embodiment, the device is sized so that is will not extend significantly beyond the synovium. Generally, and by way of example only, the length and width of the meniscal repair device can be in the range of about 0.5 to 5 cm.

In one embodiment, the tissue repair scaffold can be pre-sized for defects or tears within the meniscus, or alternatively, the device can be oversized and cut to fit within a defect site. For example, a surgeon can view the defect site, or an image of the defect, and cut the meniscal repair device so that the scaffold is of an appropriate size to fit within a meniscal defect while the conduit flap is able to reach the synovium.

A person skilled in the art will appreciate that scaffold 22 and conduit flap 24 can be mated by a variety of techniques including suturing, heat sealing, chemical bonding, solvent bonding, adhesive bonding, fold or roll sealing, mechanical pressing, etc. As an example, a portion of the conduit flap can be folded against the scaffold and secured to the scaffold at a desired location. In one embodiment, the scaffold and conduit flap are preferably sutured together.

In an alternative embodiment, the scaffold and conduit flap can be formed from a single piece of material and trimmed, either before or during surgery, to a desired shape and size. The single piece is then preferably folded into the desired arrangement, such as, for example folded into an "L" shape.

Figure 6:
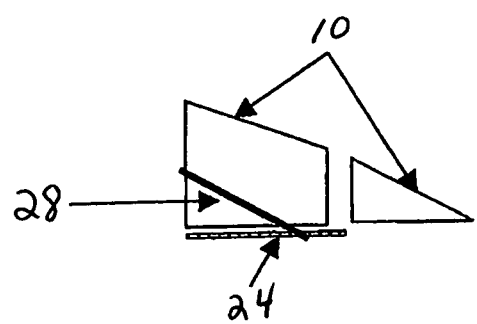
FIG. 6 is a side view of another embodiment of a meniscal repair device in accordance with the present invention.
Figure 7:
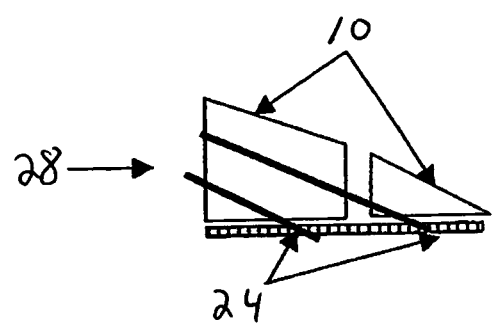
FIG. 7 is a side view of a meniscal repair device in accordance with another embodiment of the present invention.

In another embodiment of the device of the present invention, the cell growth conduit flap can be used without scaffold 20. In some cases, treating a meniscal tear does not require placing a tissue repair scaffold in the tissue defect, and only a conduit flap is used to provide a meniscal tear with biological materials. FIG. 6 illustrates the use of only conduit flap 24, with the conduit flap arranged between the synovium and tissue defect 21. Alternatively, the conduit flap can be adapted to extend from the synovium to an area beyond the tissue defect as shown in FIG. 7.

The materials used to form the tissue scaffold and conduit flap of the meniscal repair device can vary, as long as they provide sufficient strength to withstand the stresses required to support a repaired meniscal tear. Moreover, the materials used to construct the device are preferably biocompatible and cause little or no foreign body reaction. The scaffold and conduit flap can be constructed of the same or different biocompatible materials.

Sufficient strength and physical properties can be developed in the meniscal repair device through the selection of materials used to form the device, and the process used to manufacture the device. In an exemplary embodiment, the device is formed from a bioresorbable or bioabsorbable material, and more preferably from a bioresorbable or bioabsorbable material that has the ability to resorb in a timely fashion in the body environment. For example, bioresorbable or bioabsorbable material can preferably resorb in less than a year.

In one embodiment of the present invention, the meniscal repair device can be formed from a biocompatible polymer. A variety of biocompatible polymers can be used to make the conduit flap or scaffold according to the present invention. The biocompatible polymers can be synthetic polymers, natural polymers or combinations thereof. As used herein the term "synthetic polymer" refers to polymers that are not found in nature, even if the polymers are made from naturally occurring biomaterials. The term "natural polymer" refers to polymers that are naturally occurring.

In embodiments where the tissue repair device includes at least one synthetic polymer, suitable biocompatible synthetic polymers can include polymers selected from the group consisting of aliphatic polyesters, poly(amino acids), copoly (ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, poly(propylene fumarate), polyurethane, poly(ester urethane), poly(ether urethane), and blends and copolymers thereof. Suitable synthetic polymers for use in the present invention can also include biosynthetic polymers based on sequences found in collagen, laminin, glycosaminoglycans, elastin, thrombin, fibronectin, starches, poly(amino acid), gelatin, alginate, pectin, fibrin, oxidized cellulose, chitin, chitosan, tropoelastin, hyaluronic acid, silk, ribonucleic acids, deoxyribonucleic acids, polypeptides, proteins, polysaccharides, polynucleotides and combinations thereof.

For the purpose of this invention aliphatic polyesters include, but are not limited to, homopolymers and copolymers of lactide (which includes lactic acid, D-, L- and meso lactide); glycolide (including glycolic acid); ε-caprolactone; p-dioxanone (1,4-dioxan-2-one); trimethylene carbonate (1,3-dioxan-2-one); alkyl derivatives of trimethylene carbonate; δ-valerolactone; β-butyrolactone; γ-butyrolactone; ε-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one;

6,6-dimethyl-1,4-dioxan-2-one; 2,5-diketomorpholine; pivalolactone; α,α diethylpropiolactone; ethylene carbonate; ethylene oxalate; 3-methyl-1,4-dioxane-2,5-dione; 3,3-diethyl-1,4-dioxan-2,5-dione; 6,6-dimethyl-dioxepan-2-one; 6,8-dioxabicycloctane-7-one and polymer blends thereof. Aliphatic polyesters used in the present invention can be homopolymers or copolymers (random, block, segmented, tapered blocks, graft, triblock, etc.) having a linear, branched or star structure. Other useful polymers include polyphosphazenes, co-, ter- and higher order mixed monomer based polymers made from L-lactide, D,L-lactide, lactic acid, glycolide, glycolic acid, para-dioxanone, trimethylene carbonate and ε-caprolactone.

In one embodiment, the meniscal repair device includes at least one natural polymer. Suitable examples of natural polymers include, but are not limited to, fibrin-based materials, collagen-based materials, hyaluronic acid-based materials, glycoprotein-based materials, cellulose-based materials, silks and combinations thereof.

In yet another embodiment, the meniscal repair device includes a naturally occurring extracellular matrix material ("ECM"), such as that found in the stomach, bladder, alimentary, respiratory, urinary, integumentary, genital tracts, or liver basement membrane of animals. Preferably, the ECM is derived from the alimentary tract of mammals, such as cows, sheeps, dogs, cats, and most preferably from the intestinal tract of pigs. The ECM is preferably small intestine submucosa ("SIS"), which can include the tunica submucosa, along with basilar portions of the tunica mucosa, particularly the lamina muscularis mucosa and the stratum compactum.

In other embodiments of the present invention, the meniscal repair device can be formed from elastomeric copolymers such as, for example, polymers having an inherent viscosity in the range of about 1.2 dL/g to 4 dL/g, more preferably about 1.2 dL/g to 2 dL/g, and most preferably about 1.4 dL/g to 2 dL/g as determined at 25° C. in a 0.1 gram per deciliter (g/dL) solution of polymer in hexafluoroisopropanol (HFIP). Suitable elastomers also preferably exhibit a high percent elongation and a low modulus, while possessing good tensile strength and good recovery characteristics. In the preferred embodiments of this invention, the elastomer exhibits a percent elongation greater than about 200 percent and preferably greater than about 500 percent. In addition to these elongation and modulus properties, the elastomers should also have a tensile strength greater than about 500 psi, preferably greater than about 1,000 psi, and a tear strength of greater than about 50 lbs/inch, preferably greater than about 80 lbs/inch.

Exemplary biocompatible elastomers include, but are not limited to, elastomeric copolymers of ε-caprolactone and glycolide with a mole ratio of ε-caprolactone to glycolide of from about 35:65 to about 65:35, more preferably from 45:55 to 35:65; elastomeric copolymers of ε-caprolactone and lactide (including L-lactide, D-lactide, blends thereof, and lactic acid polymers and copolymers) where the mole ratio of ε-caprolactone to lactide is from about 95:5 to about 30:70 and more preferably from 45:55 to 30:70 or from about 95:5 to about 85:15; elastomeric copolymers of p-dioxanone (1,4-dioxan-2-one) and lactide (including L-lactide, D-lactide, blends thereof, and lactic acid polymers and copolymers) where the mole ratio of p-dioxanone to lactide is from about 40:60 to about 60:40; elastomeric copolymers of ε-caprolactone and p-dioxanone where the mole ratio of ε-caprolactone to p-dioxanone is from about from 30:70 to about 70:30; elastomeric copolymers of p-dioxanone and trimethylene carbonate where the mole ratio of p-dioxanone to trimethylene carbonate is from about 30:70 to about 70:30; elastomeric copolymers of trimethylene carbonate and glycolide (including polyglycolic acid) where the mole ratio of trimethylene carbonate to glycolide is from about 30:70 to about 70:30; elastomeric copolymers of trimethylene carbonate and lactide (including L-lactide, D-lactide, blends thereof, and lactic acid polymers and copolymers) where the mole ratio of trimethylene carbonate to lactide is from about 30:70 to about 70:30; and blends thereof. Other examples of suitable biocompatible elastomers are described in U.S. Pat. No. 5,468,253.

In another embodiment of the present invention, the meniscal repair device can be formed from an elastomer that is a copolymer of 35:65 ε-caprolactone and glycolide, formed in a dioxane solvent and including a polydioxanone mesh. In another embodiment, the elastomer used to form the tissue repair device can be a copolymer of 40:60 ε-caprolactone and lactide with a polydioxanone mesh. In yet another embodiment, the elastomer is a 50:50 blend of a 35:65 copolymer of ε-caprolactone and glycolide and 40:60 copolymer of ε-caprolactone and lactide. The polydioxanone mesh may be in the form of a one layer thick two-dimensional mesh or a multi-layer thick three-dimensional mesh.

In yet another embodiment of the present invention, the meniscal repair device can be formed from a polymeric foam component having pores with an open cell pore structure. The pore size can vary, but preferably, the pores are sized to allow tissue ingrowth. More preferably, the pore size is in the range of about 50 to 1000 microns, and even more preferably, in the range of about 50 to 500 microns. The polymeric foam component can, optionally, contain a reinforcing component, such as for example, the textiles disclosed above. In some embodiments where the polymeric foam component contains a reinforcing component, the foam component can be integrated with the reinforcing component such that the pores of the foam component penetrate the mesh of the reinforcing component and interlock with the reinforcing component.

It may also be desirable to use polymer blends to form meniscal repair devices which transition from one composition to another composition in a gradient-like architecture. For example, by blending an elastomer of ε-caprolactone-co-glycolide with ε-caprolactone-co-lactide (e.g., with a mole ratio of about 5:95) a device may be formed that transitions from a softer spongy material to a stiffer more rigid material. Clearly, one skilled in the art will appreciate that other polymer blends may be used for similar gradient effects, or to provide different gradients (e.g., different absorption profiles, stress response profiles, different degrees of elasticity, or different porosities).

One of ordinary skill in the art will appreciate that the selection of a suitable material for forming the biocompatible tissue repair device of the present invention depends on several factors. These factors include in vivo mechanical performance; cell response to the material in terms of cell attachment, proliferation, migration and differentiation; biocompatibility; and optionally, bioabsorption (or bio-degradation) kinetics. Other relevant factors include the chemical composition, spatial distribution of the constituents, the molecular weight of the polymer, and the degree of crystallinity.

The differences in the absorption time under in vivo conditions can also be the basis for combining two different copolymers when forming the device of the present invention. For example, a copolymer of 35:65 ε-caprolactone and glycolide (a relatively fast absorbing polymer) can be blended with 40:60 ε-caprolactone and L-lactide copolymer (a relatively slow absorbing polymer) to form a biocompatible meniscal repair device. Depending upon the processing technique used, the two constituents can be either randomly interconnected bicontinuous phases, or the constituents could have a gradient-like architecture in the form of a laminate-type composite with a well integrated interface between the two constituent layers.

The meniscal repair device used to form the composite implant can also include a reinforcing material comprised of any absorbable or non-absorbable textile having, for example, woven, knitted, warped knitted (i.e., lace-like), non-woven, and braided structures. In one embodiment, the reinforcing material has a mesh-like structure. In any of the above structures, mechanical properties of the material can be altered by changing the density or texture of the material, the type of knit or weave of the material, the thickness of the material, or by embedding particles in the material. The mechanical properties of the material may also be altered by creating sites within the mesh where the fibers are physically bonded with each other or physically bonded with another agent, such as, for example, an adhesive or a polymer.

The fibers used to make the reinforcing component can include monofilaments, yarns, threads, braids, or bundles of fibers. These fibers can be made of any biocompatible material including bioabsorbable materials such as polylactic acid (PLA), polyglycolic acid (PGA), polycaprolactone (PCL), polydioxanone (PDO), trimethylene carbonate (TMC), copolymers or blends thereof. These fibers can also be made from any biocompatible materials based on natural polymers including silk and collagen-based materials. These fibers can also be made of any biocompatible fiber that is nonresorbable, such as, for example, polyethylene, polyethylene terephthalate, poly(tetrafluoroethylene), polycarbonate, polypropylene and poly(vinyl alcohol). In one embodiment, the fibers are formed from 95:5 copolymer of lactide and glycolide.

The meniscal repair device, as well as any reinforcing material, may also be formed from a thin, perforation-containing elastomeric sheet with pores or perforations to allow tissue ingrowth. Such a sheet could be made of blends or copolymers of polylactic acid (PLA), polyglycolic acid (PGA), polycaprolactone (PCL), and polydioxanone (PDO).

A person skilled in the art will appreciate that one or more layers of the reinforcing material may be used to reinforce the composite implant of the invention. In addition, biodegradable textiles, such as, for example, meshes, of the same structure and chemistry or different structures and chemistries can be overlaid on top of one another to fabricate biocompatible meniscal repair devices with superior mechanical strength.

In one embodiment, the meniscal repair device of the present invention includes a high-density, nonwoven polymeric material. Preferably, the nonwoven material includes flexible, porous structures produced by interlocking layers or networks of fibers, filaments, or film-like filamentary structures. The polymeric material used to construct the nonwoven can include the bioabsorbable synthetic polymer materials listed above. The nonwoven may additionally include a biocompatible foam for reinforcing the scaffold. Exemplary materials are disclosed in U.S. patent application Ser. No. 10/828,838 entitled "Nonwoven Tissue Scaffold", filed concurrently herewith.

The meniscal repair device of the present invention can preferably include a source of viable tissue. The source of viable tissue can vary, and the tissue source can have a variety of configurations. In one embodiment, however, the tissue is in the form of finely minced tissue fragments, which enhance the effectiveness of the regrowth and healing response. In another embodiment, the viable tissue can be in the form of a tissue slice or strip that harvested from healthy tissue that contains viable cells capable of tissue regeneration and/or remodeling, as described in U.S. patent application Ser. No. 10/729,046 filed Dec. 5, 2003 and entitled "Viable Tissue Repair Implants and Methods of Use." The tissue slice is preferably harvested to have a geometry that is suitable for implantation at the site of the injury or defect, and the harvested tissue slice is preferably dimensioned to allow the viable cells contained within the tissue slice to migrate out and proliferate and integrate with tissue surrounding the repair site.

The term "slice," as used herein, refers to a thin section, strip or sliver derived from any of the tissue types described above and used to construct the tissue implant. Preferably, the tissue slice has a thickness less than about 1 mm, and more preferably has a thickness in the range of about 200 µm to about 500 µm. A thin profile ensures proper migration of the cells out of the tissue slice. It is understood, however, that the tissue slice can have any length or width appropriate for implantation at the defect, since these parameters do not greatly affect cell migration out of the tissue slice.

Where a tissue fragment is used with the device of the present invention, the particle size of each tissue fragment can also vary. By way of non-limiting example, the tissue size can be in the range of about 0.1 and 3 mm$^3$, in the range of about 0.5 and 1 mm$^3$, in the range of about 1 to 2 mm$^3$, or in the range of about 2 to 3 mm$^3$, but preferably the tissue particle is less than 1 mm$^3$.

Suitable tissue from which the tissue source can be derived includes, for example, cartilage tissue, meniscal tissue, ligament tissue, tendon tissue, skin tissue, bone tissue, muscle tissue, periosteal tissue, pericardial tissue, synovial tissue, nerve tissue, fat tissue, kidney tissue, bone marrow, liver tissue, bladder tissue, pancreas tissue, spleen tissue, intervertebral disc tissue, embryonic tissue, periodontal tissue, vascular tissue, blood, and combinations thereof. The tissue used to construct the tissue implant can be autogeneic tissue, allogeneic tissue, or xenogeneic tissue. In a preferred embodiment, the viable tissue is autogeneic meniscal tissue.

The viable tissue can also optionally be combined with a variety of other materials, including carriers, such as a gel-like carrier or an adhesive. By way of non-limiting example, the gel-like carrier can be a biological or synthetic hydrogel such as hyaluronic acid, fibrin glue, fibrin clot, collagen gel, collagen-based adhesive, alginate gel, crosslinked alginate, chitosan, synthetic acrylate-based gels, platelet rich plasma (PRP), platelet poor plasma (PPP), PRP clot, PPP clot, blood, blood clot, blood component, blood component clot, Matrigel, agarose, chitin, chitosan, polysaccharides, poly(oxyalkylene), a copolymer of poly(ethylene oxide)-poly(propylene oxide), poly(vinyl alcohol), laminin, elasti, proteoglycans, solubilized basement membrane, or combinations thereof. Suitable adhesives include, but are not limited to, hyaluronic acid, fibrin glue, fibrin clot, collagen gel, collagen-based adhesive, alginate gel, crosslinked alginate, gelatin-resorcin-formalin-based adhesive, mussel-based adhesive, dihydroxyphenylalanine (DOPA)-based adhesive, chitosan, transglutaminase, poly(amino acid)-based adhesive, cellulose-based adhesive, polysaccharide-based adhesive, synthetic acrylate-based adhesives, platelet rich plasma (PRP), platelet poor plasma (PPP), PRP clot, PPP clot, blood, blood clot, blood component, blood component clot, polyethylene glycol-based adhesive, Matrigel, Monostearoyl Glycerol co-Succinate (MGSA), Monostearoyl Glycerol co-Succinate/polyethylene glycol (MGSA/PEG) copolymers, laminin, elastin, proteoglycans, and combinations thereof.

The viable tissue can also be contacted with a matrix-digesting enzyme to facilitate tissue migration out of the extracellular matrix surrounding the viable tissue. The enzymes can be used to increase the rate of cell migration out of the extracellular matrix and into the tissue defect or injury, or scaffold material. Suitable matrix-digesting enzymes that can be used in the present invention include, but are not limited to, collagenase, chondroitinase, trypsin, elastase, hyaluronidase, peptidase, thermolysin, matrix metalloproteinase, gelatinase and protease. Preferably, the concentration of minced tissue particles in the gel-carrier is in the range of approximately 1 to 1000 mg/cm$^3$, and more preferably in the range of about 1 to 200 mg/cm$^3$.

In another embodiment of the present invention, a bioactive agent may be incorporated within and/or applied to the meniscal repair device, and/or it can be applied to the viable tissue. Preferably, the bioactive agent is incorporated within, or coated on, the device prior to the addition of viable tissue. The bioactive agent(s) can be selected from among a variety of effectors that, when present at the site of injury, promote healing and/or regeneration of the affected tissue. In addition to being compounds or agents that actually promote or expedite healing, the effectors may also include compounds or agents that prevent infection (e.g., antimicrobial agents and antibiotics), compounds or agents that reduce inflammation (e.g., anti-inflammatory agents), compounds that prevent or minimize adhesion formation, such as oxidized regenerated cellulose (e.g., INTERCEED® and SURGICEL®, available from Ethicon, Inc.), hyaluronic acid, and compounds or agents that suppress the immune system (e.g., immunosuppressants).

By way of non-limiting example, other types of effectors present within the implant of the present invention can include heterologous or autologous growth factors, proteins (including matrix proteins), peptides, antibodies, enzymes, platelets, platelet rich plasma, glycoproteins, hormones, cytokines, glycosaminoglycans, nucleic acids, analgesics, viruses, virus particles, and cell types. It is understood that one or more effectors of the same or different functionality may be incorporated within the implant.

Examples of suitable effectors include the multitude of heterologous or autologous growth factors known to promote healing and/or regeneration of injured or damaged tissue. These growth factors can be incorporated directly into the meniscal repair device, or alternatively, the device can include a source of growth factors, such as for example, platelets. "Bioactive agents," as used herein, can include one or more of the following: chemotactic agents; therapeutic agents (e.g., antibiotics, steroidal and non-steroidal analgesics and anti-inflammatories, anti-rejection agents such as immunosuppressants and anti-cancer drugs); various proteins (e.g., short term peptides, bone morphogenic proteins, glycoprotein and lipoprotein); cell attachment mediators; biologically active ligands; integrin binding sequence; ligands; various growth and/or differentiation agents and fragments thereof (e.g., epidermal growth factor (EGF), hepatocyte growth factor (HGF), vascular endothelial growth factors (VEGF), fibroblast growth factors (e.g., bFGF), platelet derived growth factors (PDGF), insulin derived growth factor (e.g., IGF-1, IGF-II) and transforming growth factors (e.g., TGF-β I-III), parathyroid hormone, parathyroid hormone related peptide, bone morphogenic proteins (e.g., BMP-2, BMP-4; BMP-6; BMP-12), sonic hedgehog, growth differentiation factors (e.g., GDF5, GDF6, GDF8), recombinant human growth factors (e.g., MP52), cartilage-derived morphogenic proteins (CDMP-1)); small molecules that affect the upregulation of specific growth factors; tenascin-C; hyaluronic acid; chondroitin sulfate; fibronectin; decorin; thromboelastin; thrombin-derived peptides; heparin-binding domains; heparin; heparan sulfate; DNA fragments and DNA plasmids. Suitable effectors likewise include the agonists and antagonists of the agents described above. The growth factor can also include combinations of the growth factors described above. In addition, the growth factor can be autologous growth factor that is supplied by platelets in the blood. In this case, the growth factor from platelets will be an undefined cocktail of various growth factors. If other such substances have therapeutic value in the orthopaedic field, it is anticipated that at least some of these substances will have use in the present invention, and such substances should be included in the meaning of "bioactive agent" and "bioactive agents" unless expressly limited otherwise.

Biologically derived agents, suitable for use as effectors, include one or more of the following: bone (autograft, allograft, and xenograft) and derivates of bone; cartilage (autograft, allograft and xenograft), including, for example, meniscal tissue, and derivatives; ligament (autograft, allograft and xenograft) and derivatives; derivatives of intestinal tissue (autograft, allograft and xenograft), including for example submucosa; derivatives of stomach tissue (autograft, allograft and xenograft), including for example submucosa; derivatives of bladder tissue (autograft, allograft and xenograft), including for example submucosa; derivatives of alimentary tissue (autograft, allograft and xenograft), including for example submucosa; derivatives of respiratory tissue (autograft, allograft and xenograft), including for example submucosa; derivatives of genital tissue (autograft, allograft and xenograft), including for example submucosa; derivatives of liver tissue (autograft, allograft and xenograft), including for example liver basement membrane; derivatives of skin tissue; platelet rich plasma (PRP), platelet poor plasma, bone marrow aspirate, demineralized bone matrix, insulin derived growth factor, whole blood, fibrin and blood clot. Purified ECM and other collagen sources are also appropriate biologically derived agents. If other such substances have therapeutic value in the orthopaedic field, it is anticipated that at least some of these substances will have use in the present invention, and such substances should be included in the meaning of "biologically derived agent" and "biologically derived agents" unless expressly limited otherwise.

Biologically derived agents also include bioremodelable collageneous tissue matrices. The terms "bioremodelable collageneous tissue matrix" and "naturally occurring bioremodelable collageneous tissue matrix" include matrices derived from native tissue selected from the group consisting of skin, artery, vein, pericardium, heart valve, dura mater, ligament, bone, cartilage, bladder, liver, stomach, fascia and intestine, whatever the source. Although the term "naturally occurring bioremodelable collageneous tissue matrix" is intended to refer to matrix material that has been cleaned, processed, sterilized, and optionally crosslinked, it is not within the definition of a naturally occurring bioremodelable collageneous tissue matrix to purify the natural fibers and reform a matrix material from purified natural fibers.

The proteins that may be present within the implant include proteins that are secreted from a cell or other biological source, such as for example, a platelet, which is housed within the implant, as well as those that are present within the implant in an isolated form. The isolated form of a protein typically is one that is about 55% or greater in purity, i.e., isolated from other cellular proteins, molecules, debris, etc. More preferably, the isolated protein is one that is at least 65% pure, and most preferably one that is at least about 75 to 95% pure. Notwithstanding the above, one of ordinary skill in the art will appreciate that proteins having a purity below about 55% are still considered to be within the scope of this invention. As used herein, the term "protein" embraces glycoproteins, lipoproteins, proteoglycans, peptides, and fragments thereof. Examples of proteins useful as effectors include, but are not limited to, pleiotrophin, endothelin, tenascin, fibronectin, fibrinogen, vitronectin, V-CAM, I-CAM, N-CAM, selectin, cadherin, integrin, laminin, actin, myosin, collagen, microfilament, intermediate filament, antibody, elastin, fibrillin, and fragments thereof.

Glycosaminoglycans, highly charged polysaccharides which play a role in cellular adhesion, may also serve as effectors according to the present invention. Exemplary glycosaminoglycans useful as effectors include, but are not limited to, heparan sulfate, heparin, chondroitin sulfate, dermatan sulfate, keratan sulfate, hyaluronan (also known as hyaluronic acid), and combinations thereof.

The meniscal repair device of the present invention can also have cells incorporated therein to serve as effectors. Suitable cell types that can serve as effectors according to this invention include, but are not limited to, osteocytes, osteoblasts, osteoclasts, fibroblasts, stem cells, pluripotent cells, chondrocyte progenitors, chondrocytes, endothelial cells, macrophages, leukocytes, adipocytes, monocytes, plasma cells, mast cells, umbilical cord cells, stromal cells, mesenchymal stem cells, epithelial cells, myoblasts, tenocytes, ligament fibroblasts, neurons, bone marrow cells, synoviocytes, embryonic stem cells; precursor cells derived from adipose tissue; peripheral blood progenitor cells; stem cells isolated from adult tissue; genetically transformed cells; a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells. If other cells are found to have therapeutic value in the orthopaedic field, it is anticipated that at least some of these cells will have use in the present invention, and such cells should be included within the meaning of "cell" and "cells" unless expressly limited.

Cells typically have at their surface receptor molecules which are responsive to a cognate ligand (e.g., a stimulator). A stimulator is a ligand which when in contact with its cognate receptor induce the cell possessing the receptor to produce a specific biological action. For example, in response to a stimulator (or ligand) a cell may produce significant levels of secondary messengers, like $Ca^{+2}$, which then will have subsequent effects upon cellular processes such as the phosphorylation of proteins, such as (keeping with our example) protein kinase C. In some instances, once a cell is stimulated with the proper stimulator, the cell secretes a cellular messenger usually in the form of a protein (including glycoproteins, proteoglycans, and lipoproteins). This cellular messenger can be an antibody (e.g., secreted from plasma cells), a hormone, (e.g., a paracrine, autocrine, or exocrine hormone), a cytokine, or natural or synthetic fragments thereof.

The meniscal repair device of the invention can also be used in gene therapy techniques in which nucleic acids, viruses, or virus particles deliver a gene of interest, which encodes at least one gene product of interest, to specific cells or cell types. Accordingly, the biological effector can be a nucleic acid (e.g., DNA, RNA, or an oligonucleotide), a virus, a virus particle, or a non-viral vector. The viruses and virus particles may be, or may be derived from, DNA or RNA viruses. The gene product of interest is preferably selected from the group consisting of proteins, polypeptides, interference ribonucleic acids (iRNA) and combinations thereof.

Once the applicable nucleic acids and/or viral agents (i.e., viruses or viral particles) are incorporated into the meniscal repair device, the device can then be implanted to elicit a type of biological response. The nucleic acid or viral agent can then be taken up by the cells and any proteins that they encode can be produced locally by the cells. In one embodiment, the nucleic acid or viral agent can be taken up by the cells within the tissue fragment of the minced tissue suspension, or, in an alternative embodiment, the nucleic acid or viral agent can be taken up by the cells in the tissue surrounding the site of the injured tissue. One skilled in the art will recognize that the protein produced can be a protein of the type noted above, or a similar protein that facilitates an enhanced capacity of the tissue to heal an injury or a disease, combat an infection, or reduce an inflammatory response. Nucleic acids can also be used to block the expression of unwanted gene product that may impact negatively on a tissue repair process or other normal biological processes. DNA, RNA and viral agents are often used to accomplish such an expression blocking function, which is also known as gene expression knock out.

One skilled in the art will appreciate that the identity of the bioactive agent may be determined by a surgeon, based on principles of medical science and the applicable treatment objectives. It is understood that the bioactive agent or effector of the tissue repair implant can be incorporated within the tissue repair device before, during, or after manufacture of the device, or before, during, or after the surgical placement of the device.

By way of example, a bioactive agent can be incorporated into the meniscal repair device by placing the meniscal repair device in a suitable container comprising the bioactive agent. After an appropriate amount time and under suitable conditions, the device will become impregnated with the bioactive agent. Alternatively, the bioactive agent can be incorporated within the meniscal repair device by, for example, using an appropriately gauged syringe to inject the biological agent(s) into the scaffold and/or conduit flap. Other methods well known to those skilled in the art can be applied in order to load the device with an appropriate bioactive agent. Such techniques include mixing, pressing, spreading, centrifuging and placing the bioactive agent into the device. Alternatively, the bioactive agent can be mixed with a gel-like carrier prior to injection into the device.

In another embodiment, a surgically implanted meniscal repair device devoid of any bioactive agent can be infused with biological agent(s), or an implant including at least one bioactive agent can be augmented with a supplemental quantity of the bioactive agent. One method of incorporating a bioactive agent within a surgically implanted device is by injection using an appropriately gauged syringe.

The amount of the bioactive agent included with a meniscal repair device will vary depending on a variety of factors, including the size of the device, the porosity, the identity of the bioactive component, and the intended purpose of the tissue repair implant. One skilled in the art can readily determine the appropriate quantity of bioactive agent to include for a given application in order to facilitate and/or expedite the healing of tissue.

After positioning the meniscal repair device of the present invention within a patient, the device is preferably fastened within the damaged or torn meniscal tissue. In one embodiment, the repair device is fixed to adjacent tissue such that the repair device is anchored in place. The repair device can be anchored to soft and/or hard tissue such as meniscal tissue or tibial tissue. In another embodiment, the repair device may additionally or alternatively be fixed to meniscal tissue to hold damaged or loose tissue in position. Joining the repair device with loose meniscal tissue provides support to the damaged tissue area and thereby facilitates rapid healing. A person skilled in the art will appreciate that a variety of techniques can be used to fix the device to hard and/or soft tissue, such as, for example, an interference fit, suture, glue, staple, tissue tack, pins, and/or other known surgical fixation techniques.

The present invention also includes methods of surgically repairing meniscal defects with the tissue repair device of the present invention by positioning at least a portion of the repair device in contact with a defect in a meniscus. In one embodiment, the scaffold is positioned in a meniscal tissue tear, and the cell growth conduit flap in positioned in contact with a tibial surface. A person skilled in the art will appreciate that contact with the tibial surface includes placing the conduit flap in proximity to the tibial surface when biological materials, such as blood, form a thin layer between the repair device and the tibial surface. The device is then fixed in position, preferably with sutures extending through the scaffold and meniscus.

The meniscal repair device can be used to fix all types of meniscal tissue defects. For example, the device can be used to repair tears such as bucket handle, longitudinal, horizontal, degenerative, radial, flap, and parrot beak tears.

In one embodiment, the method can additionally include the step of inducing bleeding at or near the tissue defect to promote the flow of biological materials necessary for regenerating meniscal tissue. Preferably, the meniscus, and/or synovium is rasped prior to implanting the tissue repair device.

Figure 5:
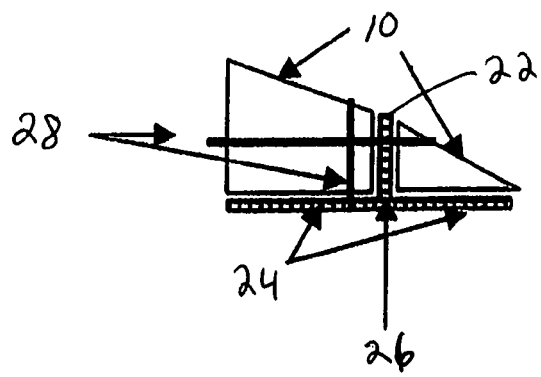
FIG. 5 is a side view of yet another embodiment of a meniscal repair device in accordance with the present invention.

After implanting the meniscal repair device, it is preferably fixed in place. In one embodiment, device 20 is sutured in place as shown in FIGS. 2-4. Sutures 28 extend through portions of the meniscus and through scaffold 22 to securely position the repair device relative to the damaged or torn meniscal tissue. Alternatively, sutures could extend through the meniscus and conduit flap 24. FIG. 5 illustrates sutures 28 fixing both the tissue scaffold and the conduit flap to meniscal tissue. Where the conduit flap is used alone, it is preferably sutured to the meniscus as illustrated in FIGS. 6 and 7.

The following non-limiting examples are illustrative of the principles and practice of this invention. Numerous additional embodiments within the scope and spirit of the invention will become apparent to those skilled in the art.

EXAMPLE

The placement of tissue implants in proximity to the synovium was compared and evaluated using a tissue repair implant constructed from a nonwoven material of 50/50 PDS/VICRYL. The implant had dimensions of approximately 11 mm×7 mm×1 mm and a density of 236.6 mg/cc.

The animals used in this study were Nubian goats. A medial approach to the stifle joint was made. The joint capsule on either side of the medial collateral ligament was incised. The medial collateral ligament was isolated and cut midsubstance. Using a biopsy punch, a full thickness defect was made in the mid-portion of the meniscus. The platelets in the blood were concentrated to create platelet rich plasma (PRP) and a clot was formed from the PRP on the tissue implant. The tissue implant with associated PRP clot was then placed in the defect as explained below.

The tissue implant was stabilized with two polypropylene horizontal mattress sutures using a modified inside-out technique. The medial collateral ligament was stabilized with two sutures anchors (Super QuickAnchor Plus with Ethibond #2, Mitek Worldwide, Norwood, Mass.) using a locking-loop suture pattern. The joint capsule was closed with a continuous suture pattern. The remaining fascial, muscular, subcutaneous, and skin layers were closed. After closing the skin, the leg was placed in a modified Schroeder-Thomas splint. A fentanyl patch, having a dose of 100 micrograms per animal, was placed on each goat at a site under the splint. The splints were removed from each animal at approximately 28 days after the surgery. For gross analysis and histopathology study, the goats were sacrificed 6 weeks after the surgery. The menisci were removed and fixed in 10% neutral buffered formalin. The samples were processed in paraffin, cut into sections and stained with Hematoxylin Eosin.

Figure 8:
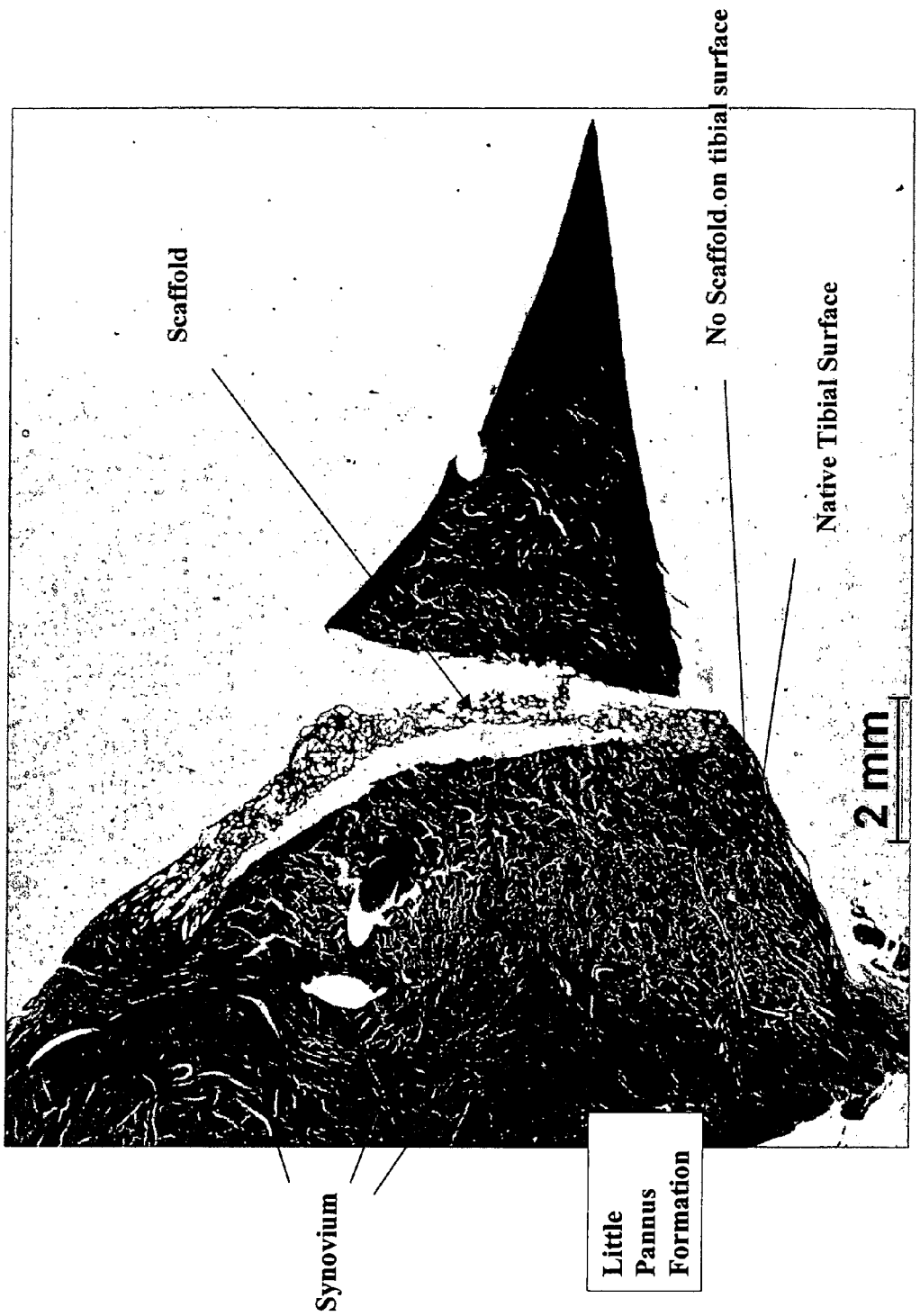
FIG. 8 is a photomicrograph of an implanted tissue repair scaffold positioned at a distance from the meniscal rim.
Figure 9:
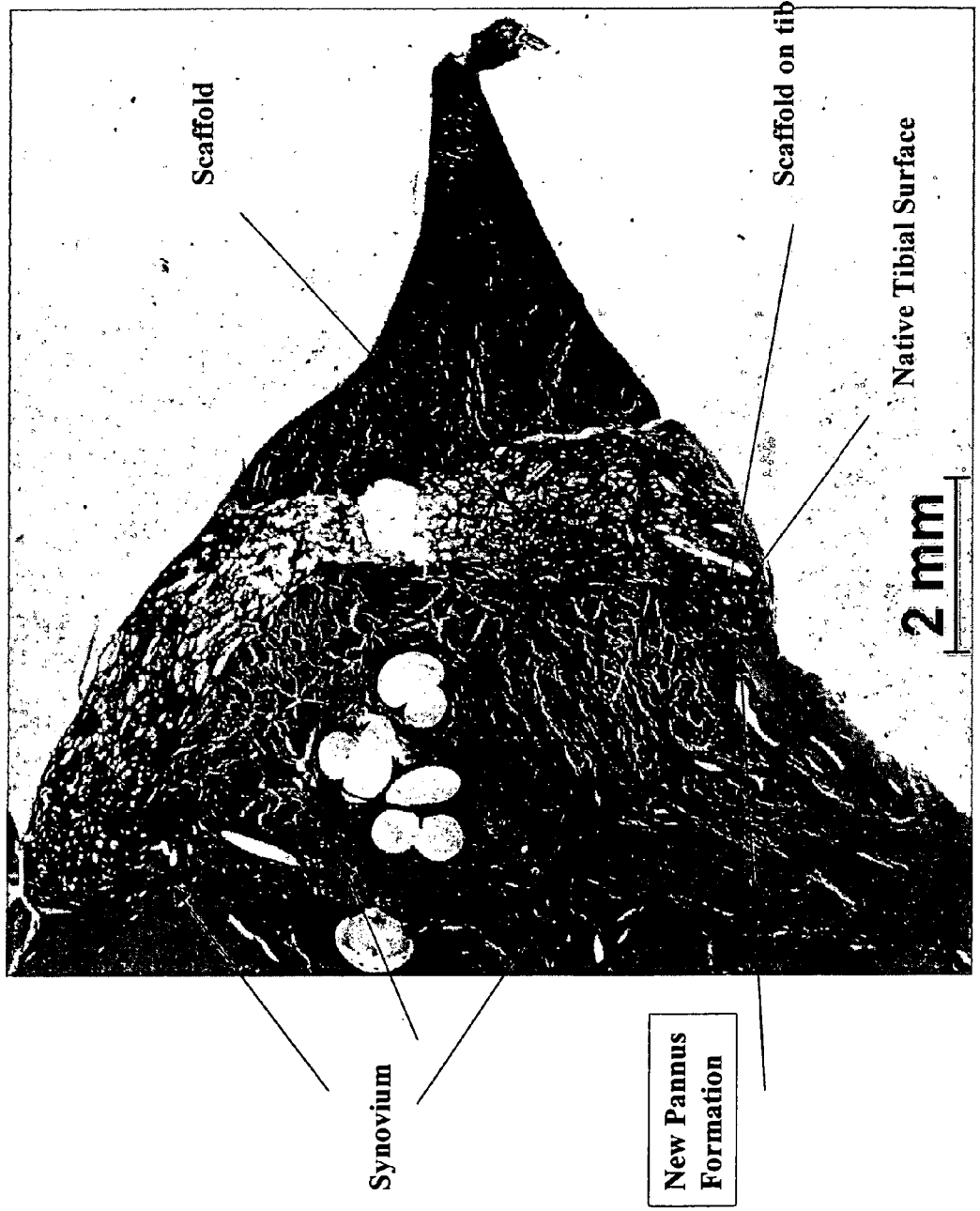
FIG. 9 is a photomicrograph of an implanted tissue repair scaffold positioned on the tibial surface in proximity to the meniscal rim.

FIGS. 8 and 9 illustrate the results of positioning tissue implants in proximity or at a distance from the synovium. In FIG. 8, the tissue implant is positioned in the meniscal defect, but does not extend onto the tibial surface. Conversely, in FIG. 9, a portion of the implant extends onto the tibial surface and contacts the synovium at the periphery of the meniscus. By positioning the implant in contact with the synovium, the meniscal defect is receiving sufficient biological material to grow cells, and thus, more pannus is formed on the tibial surface. The result is a more effective meniscal repair device.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. A method of surgically repairing meniscal defects, comprising:
   providing a tissue repair scaffold having attached thereto a cell growth conduit flap, the cell growth conduit flap extending from a first end attached to the tissue repair scaffold to a free end remote from the scaffold;
   positioning the tissue repair scaffold in contact with a defect in a meniscus while positioning the cell growth conduit flap in contact with a tibial surface and a synovium; and
   fixing the tissue repair scaffold in position,
   wherein the cell growth conduit flap comprises at least one channel extending therethrough configured to communicate cells and nutrients from the synovium to the defect in the meniscus and thereby encourage healing of the meniscus, wherein the density of the cell growth conduit flap is in the range of about 150 mg/cc to 350 mg/cc.

2. The method of claim 1, further comprising the step of rasping the meniscus before positioning the cell growth conduit flap.

3. The method of claim 1, further comprising the step of rasping the synovium before positioning the cell growth conduit flap.

4. The method of claim 1, wherein the cell growth conduit flap has a void volume in the range of about 50% to 95%.

5. The method of claim 1, wherein the at least one channel is on the surface of the cell growth conduit flap.

6. The method of claim 1, wherein the at least one channel is within the cell growth conduit flap.

7. A method of surgically repairing meniscal defects, comprising:
   providing a cell growth conduit flap;
   positioning the cell growth conduit flap in contact with a tissue defect in a meniscus and in contact with a tibial surface and a synovium; and fixing the cell growth conduit flap in position,
wherein the cell growth conduit flap comprises at least one channel extending therethrough effective to communicate cells and nutrients from the synovium to the defect in the meniscus and thereby promote healing of the meniscus, wherein the density of the cell growth conduit flap is in the range of about 150 mg/cc to 350 mg/cc.

8. The method of claim 7, wherein the cell growth conduit flap provides a conduit that enables cells and nutrients to travel from the synovium to the tissue defect in a meniscus.

9. The method of claim 7, further comprising the step of rasping the meniscus before positioning the cell growth conduit flap.

10. The method of claim 7, further comprising the step of rasping the synovium before positioning the cell growth conduit flap.

11. The method of claim 7, wherein the cell growth conduit flap has a void volume in the range of about 50% to 95%.

12. The method of claim 7, wherein the at least one channel is on the surface of the cell growth conduit flap.

13. The method of claim 7, wherein the at least one channel is within the cell growth conduit flap.

* * * * *